United States Patent [19]

Saito

[11] Patent Number: 5,445,920
[45] Date of Patent: Aug. 29, 1995

[54] FABRICATION PROCESS OF BIOSENSOR

[75] Inventor: Atsushi Saito, Tokyo, Japan

[73] Assignee: NEC Corporation, Tokyo, Japan

[21] Appl. No.: 190,371

[22] Filed: Feb. 2, 1994

[30] Foreign Application Priority Data

Feb. 18, 1993 [JP] Japan .................. 5-028345

[51] Int. Cl.$^6$ .................................. G03F 7/00
[52] U.S. Cl. .................. 430/311; 430/315; 430/320; 430/324
[58] Field of Search ........... 430/311, 315, 319, 320, 430/324, 329

[56] References Cited

U.S. PATENT DOCUMENTS

| 4,909,921 | 3/1990 | Ito ........................ 204/403 |
| 5,063,081 | 11/1991 | Cozzette ................. 427/2 |
| 5,118,404 | 6/1992 | Saito ...................... 204/403 |

FOREIGN PATENT DOCUMENTS 55-162051 12/1980 Japan .
3-65645 3/1991 Japan .

OTHER PUBLICATIONS

"Whole Blood Glucose Enzyme Electrode", *The Electrochemical Society Extended Abstracts*, Abstract No. 1682, vol. 87, No. 2, Oct. 1987, p. 2276, Genshaw et al.

*Primary Examiner*—Kathleen Duda
*Attorney, Agent, or Firm*—Young & Thompson

[57] ABSTRACT

A process is provided for the mass-fabrication of biosensors having a permeation-restricted membrane of uniform quality. A photoresist is coated over an entire surface of a wafer on which at least two pairs of electrochemical transducer devices are arranged together with electrode(s) as many as needed. The photoresist is removed at predetermined areas by photolithography. The entire surface of the wafer is next coated with a liquid coating formulation of a crosslinkable polymer and a crosslinking agent, followed by the gelation of the coating formulation. Further, a liquid coating formulation of a crosslinkable polymer and a crosslinking agent, the coating formulation preferably containing a silicone, is coated over the entire surface of the wafer and is then caused to gel. The wafer is next treated in an organic solvent to dissolve the photoresist, so that an enzyme-free, crosslinked membrane and a permeation-restricted membrane are formed. Using an enzyme-containing liquid coating formulation of a crosslinkable polymer and a crosslinking agent, an enzyme-immobilized membrane and a permeation-restricted membrane are next formed likewise. The resulting wafer is finally cut functional unit by functional unit into chips.

16 Claims, 6 Drawing Sheets

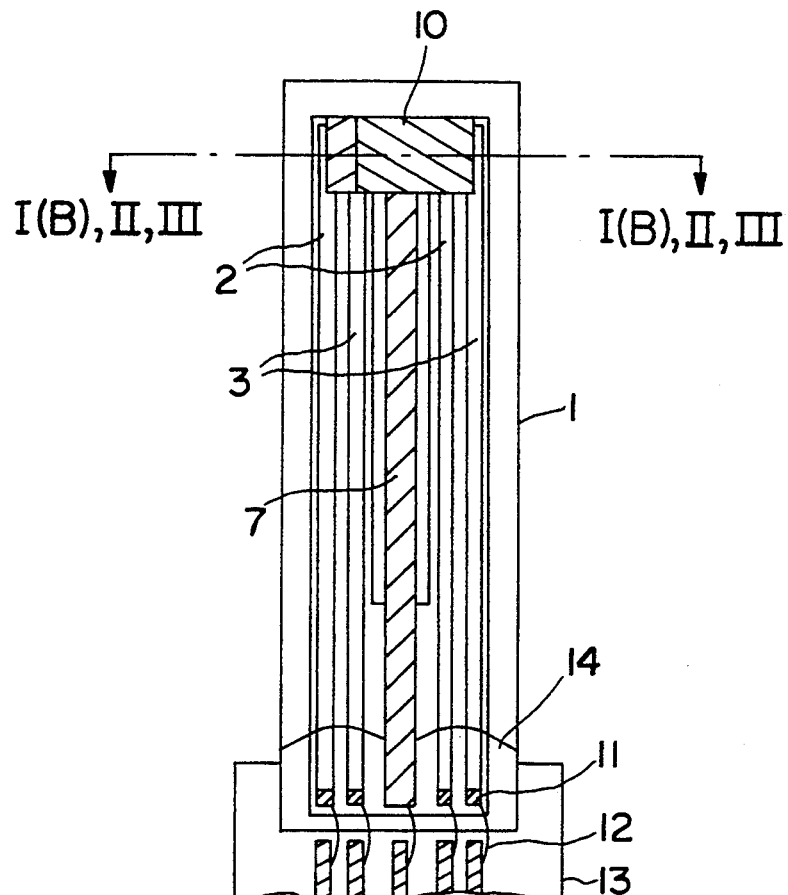
FIG.I(A)
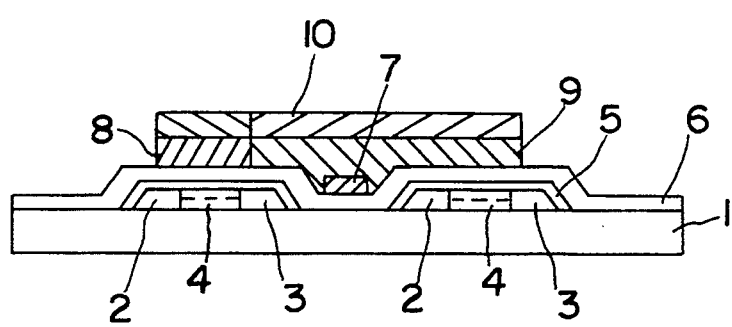
FIG.I(B)

FABRICATION PROCESS OF BIOSENSOR

BACKGROUND OF THE INVENTION a) Field of the Invention

This invention relates to a process for the fabrication of biosensors, especially enzyme sensors. In particular, this invention is concerned with a process for fabricating biosensors, which have a wide detection range despite of their high sensitivity, in a large quantity and with uniform quality. Sensors of such characteristics are extremely useful, for example, for the determination of blood glucose concentrations.

b) Description of the Related Art

As a glucose sensor of the above-described type, the one disclosed for example in Japanese Patent Laid-Open No. 162051/1980 has been used conventionally to determine the concentration of glucose in blood (blood glucose concentration). This glucose sensor is formed of a glucose-oxidase-immobilized film and a transducer.

The enzyme employed in the above glucose sensor, glucose oxidase converts glucose, which is contained in a solution, into gluconic acid and hydrogen peroxide by using oxygen. It is therefore possible to determine the concentration of glucose in the solution by various transducers, for example, by measuring a decrease of oxygen with an oxygen electrode, measuring an increase of hydrogen peroxide with a hydrogen peroxide electrode or by measuring an increase of gluconic acid with a pH electrode.

The concentration of oxygen dissolved in a sample solution to be determined is about 0.25 mM where the sample solution has been saturated with the surrounding air. To date, this dissolved oxygen concentration has acted as a limiting factor so that the measurable upper limit of a glucose sensor has been around 100 mg/dl. The blood glucose concentration of a diabetic may however reach as high as 500 mg/dl, so that no known glucose sensors can determine such glucose concentrations.

It is hence known to upwardly shift the measurable upper limit of a glucose sensor by using a glucose-permeation-restricted membrane which restricts permeation of glucose more than that of oxygen as disclosed, for example, in Japanese Patent Laid-Open No. 162051/1980, The Electrochemical Society Extended Abstracts, 87(2), 2276 (October, 1987) or Japanese Patent Laid-Open No. 65645/1991.

These related glucose sensors will be described specifically in detail with reference to drawings.

FIG. 5 shows in a readily-understandable manner a glucose sensor according to the technique disclosed in Japanese Patent Laid-Open No. 162051/1980. A platinum cathode 52 and a silver anode 53 are formed on an electrode support 51. A glucose-oxidase-immobilized membrane 54 and a selectively permeable membrane 55 are successively superposed on them. These platinum cathode, silver anode, glucose-oxidase-immobilized membrane and selectively permeable membrane are covered and fixed by an outer film 56 through which a hole is formed centrally. This sensor is arranged in a wall of a substitute blood vessel to determine the concentration of glucose in blood. The glucose and oxygen in the blood reach the glucose-oxidase-immobilized membrane 54 through the selectively permeable membrane 55. The glucose is oxidized by the glucose oxidase. Here, oxygen is consumed so that the concentration of dissolved oxygen drops. The extent of this drop is detected by an oxygen electrode formed of the platinum cathode 52 and the silver anode 53, thereby making it possible to determine the glucose concentration. Further, the permeation of glucose is restricted by the action of the selectively permeable membrane 55 so that the measurable upper limit of the glucose sensor increases to 500 mg/dl.

FIG. 6(A) illustrates the construction of electrodes in the glucose sensor disclosed in The Electrochemical Society Extended Abstracts, 87(2), 2276 (October, 1987), while FIG. 6(B) is a cross-sectional view of the glucose sensor. In FIG. 6(A), a platinum cathode 61 and a silver anode 63 are formed on an epoxy resin 62 and, as in the above-described sensor, function as an oxygen electrode. In FIG. 6(B), a glucose-oxidase-immobilized membrane 64 is formed over the platinum cathode 61 and a silicone rubber membrane 65 is formed over the glucose-oxidase-immobilized membrane. Upon determination of the concentration of glucose in blood, the silicone rubber membrane 65 functions as a permeation-restricted membrane to restrict permeation of the glucose, so that the measurable upper limit of the sensor is shifted upwardly. In the case of this sensor, the glucose-oxidase-immobilized membrane 64 has been formed by applying dropwise a liquid coating formulation of glucose oxidase and glutaraldehyde while the silicone rubber membrane 65 has been formed by applying dropwise a silicone emulsion.

Further, U.S. Pat. No. 5,118,404 of the present inventor also discloses an enzyme sensor equipped with a permeation-restricted membrane.

In the fabrication of each of these glucose sensors, it was possible to form the permeation-restricted membrane by directly applying a permeation-restricted membrane, which had been produced in advance, to a surface of the sensor as shown in FIG. 5 when the transducer was large. Any attempt to miniaturize the transducer, however, made it extremely difficult to apply a pre-formed permeation-restricted membrane in the above-described manner. Sensors have therefore been fabricated one by one by applying a liquid coating formulation of raw materials for the permeation-restricted membrane on each transducer and then drying the thus-applied coating formulation as illustrated in FIG. 6(A) and FIG. 6(B). The thickness and properties of each permeation-restricted membrane significantly affect the response of the resulting glucose sensor. Nevertheless, it is difficult to obtain membranes of uniform quality as long as they are formed by a coating technique. Such conventional glucose sensors therefore have widely varying characteristic values and have a low non-defective percentage. Further, they require substantial time and labor because they are fabricated one by one.

There is accordingly an outstanding demand for the development of a process for fabricating many biosensors having uniform and high response characteristics and a wide response range while including the formation of a permeation-restricted membrane in the process.

SUMMARY OF THE INVENTION

With such current technical circumstances in view, the present invention has as a primary object the provision of a process for fabricating, without difficulties in fabrication work, many biosensors having uniform characteristic values, high sensitivity and a wide response range.

The present invention features the formation of a predetermined stacked structure by using a transducer, in which at least two pairs of electrochemical transducer devices and a pseudo-reference electrode are formed on one side of a wafer and the electrode is located substantially at a midpoint between the paired devices, and applying in combination spin-coating and photolithography in a specific order to form a permeation-restricted membrane and an enzyme-immobilized membrane.

In one aspect of the present invention, there is thus provided a process for the fabrication of plural biosensors having uniform response characteristics and a wide response range, each of said biosensors having at least two pairs of electrochemical transducer devices and a pseudo-reference electrode located substantially at a midpoint between said paired devices, said devices and said electrode being both formed on one side of a wafer, and also an enzyme-immobilized membrane and a permeation-restricted membrane, both arranged over said devices and said electrode, which comprises:

1) covering said wafer with a first photoresist coating film by a lithographic technique, which makes use of a photoresist, except for surfaces of one of said devices and of said electrode;

2) spin-coating said surfaces with an enzyme-free liquid coating formulation of an enzyme-immobilizing crosslinkable polymer;

3) spin-coating the resulting structure further with a first permeation-restricted-membrane-forming liquid coating formulation of a crosslinkable polymer;

4) causing said enzyme-free liquid coating formulation and said first liquid coating formulation to gel, whereby first and second gelled membranes are formed in a stacked form;

5) dissolving into solvent said first photoresist coating film with said first and second gelled membranes which have been formed on said first photoresist coating film, whereby said first and second gelled membranes remain in the stacked form only on said surfaces of said one device and said electrode;

6) covering a surface of the thus-obtained wafer with a second photoresist coating film by a lithographic technique, which makes use of a photoresist, except for a surface of the other one of said devices;

7) spin-coating said surface of said other device with an enzyme-containing liquid coating formulation of an enzyme-immobilizing crosslinkable polymer;

8) spin-coating the spin-coated surface of said other device further with a second permeation-restricted-membrane-forming liquid coating formulation of a crosslinkable polymer;

9) causing said enzyme-containing liquid coating formulation and said second liquid coating formulation to gel, whereby third and fourth gelled membranes are formed in a stacked form;

10) dissolving said second photoresist coating film with said third and fourth gelled membranes into solvent to allow said third and fourth gelled membranes to remain only on said surface of said other device; and then 11) cutting the thus-formed structure into pieces so that each piece includes parts of said paired electrochemical transducer devices and a part of said pseudo-reference electrode, the latter part being located substantially at the midpoint between the former parts.

In another aspect of the present invention, there is also provided a process for the fabrication of plural biosensors having uniform response characteristics and a wide response range, each of said biosensors having at least two pairs of electrochemical transducer devices and a pseudo-reference electrode located substantially at a midpoint between said paired devices, said devices and said electrode being both formed on one side of a wafer, and also an enzyme-immobilized membrane and a permeation-restricted membrane, both arranged over said devices and said electrode, which comprises:

1) covering said wafer with a first photoresist coating film by a lithographic technique, which makes use of a photoresist, except for surfaces of one of said devices and of said electrode;

2) spin-coating said surfaces with an enzyme-free liquid coating formulation of an enzyme-immobilizing crosslinkable polymer and then causing said enzyme-free liquid coating formulation to gel, whereby a first gelled membrane is formed;

3) dissolving into solvent said first photoresist coating film with said first gelled membrane which has been formed on said first photoresist coating film, whereby said first gelled membrane remains only on said surfaces of said one device and said electrode;

4) covering a surface of the thus-obtained wafer with a second photoresist coating film by a lithographic technique, which makes use of a photoresist, except for a surface of the other one of said devices;

5) spin-coating said surface of said other device with an enzyme-containing liquid coating formulation of an enzyme-immobilizing crosslinkable polymer;

6) dissolving said second photoresist coating film with said enzyme-containing liquid coating formulation of an enzyme-immobilizing crosslinkable polymer, whereby said enzyme-immobilizing crosslinkable polymer remains only on said surface of said other device;

7) spin-coating the resulting structure further with a permeation-restricted-membrane-forming liquid coating formulation of a photocrosslinkable polymer;

8) photopolymerizing the coated permeation-restricted-membrane-forming liquid coating formulation by a photolithographic technique followed by dissolving unpolymerized coating formulation into solvent, whereby a gelled membrane is formed only on said remaining first gelled membrane and enzyme-immobilizing photocrosslinkable polymer in a stacked form; and 9) cutting the thus-formed structure into pieces so that each piece includes parts of said paired electrochemical transducer devices and a part of said pseudo-reference electrode, the latter part being located substantially at the midpoint between the former parts.

Further, expressed specifically in a readily-understandable manner, the present invention also provides:

a process for fabricating glucose sensors having a glucose-oxidase-immobilized membrane and a glucose-permeation-restricted membrane successively formed on a wafer with plural electrochemical transducer devices formed thereon, which comprises the following steps: coating a photoresist over the wafer having the electrochemical transducer devices formed thereon and then removing said photoresist at predetermined areas by photolithography, spin-coating a liquid protein formulation containing glucose oxidase and a crosslinking agent on a surface of said wafer and then spin-coating a silicone emulsion on the thus spin-coated protein solution, whereby a glucose-oxidase-immobilized membrane and a silicone-membrane are formed, and treating said wafer with an organic solvent to dissolve said photoresist to allow said glucose-oxidase-immobilized membrane and said silicone membrane to remain only at areas predetermined (will hereinafter called "lift-off" technique), whereby a glucose-permeation-restricted membrane made of a homogeneous silicone membrane is formed on wafer; and a process for fabricating glucose sensors having a glucose-oxidase-immobilized membrane and a glucose-permeation-restricted membrane successively formed on a wafer with plural electrochemical transducer devices formed thereon, which comprises the following steps: coating a photoresist over the wafer having the electrochemical transducer devices formed thereon and then removing said photoresist at predetermined areas by photolithography, spin-coating a liquid protein formulation containing glucose oxidase and a crosslinking agent on a surface of said wafer to form a glucose-oxidase-immobilized membrane, treating said wafer by lift-off technique to allow said glucose-oxidase-immobilized membrane to remain on only predetermined areas, and coating a radical-modified silicone emulsion over said wafer and forming a silicone membrane at said predetermined areas by photolithography, whereby a glucose-permeation-restricted membrane made of a homogeneous silicone membrane is formed on wafer.

BRIEF DESCRIPTION OF THE DRAWINGS

FIG. 1(A) is a schematic illustration showing a glucose sensor fabricated by a process according to one embodiment of the present invention;

FIG. 1(B) is a cross-sectional view of the glucose sensor taken in the direction of arrows I(B)—I(B) of FIG. 1(A);

DESCRIPTION OF THE PREFERRED EMBODIMENTS

Figure 2A:
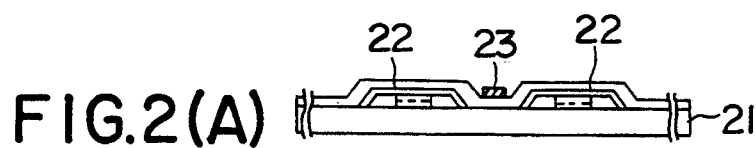
In FIG. 2, views A through H are cross-sectional views illustrating, in the order of steps, the fabrication process of the one embodiment of this invention.
Figure 2B:
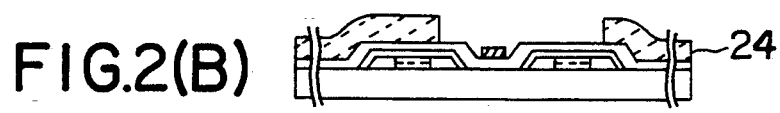
Figure 2C:
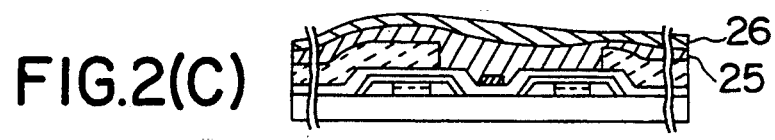
Figure 2D:
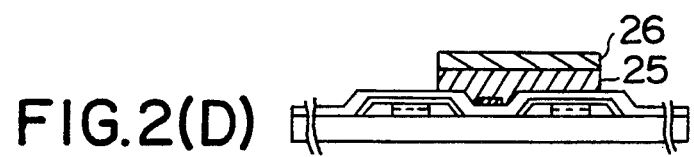
Figure 2E:
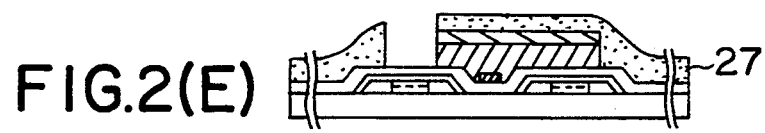
Figure 2F:
Figure 2G:
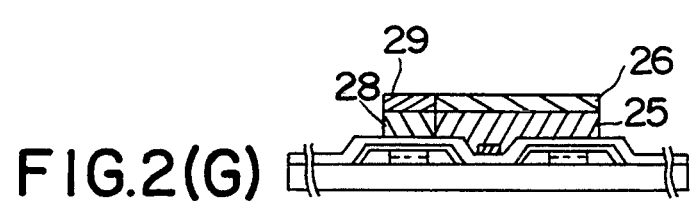
Figure 2H:
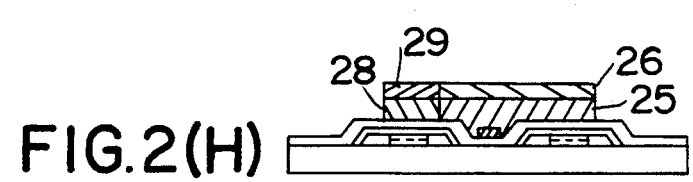
Figure 3A:
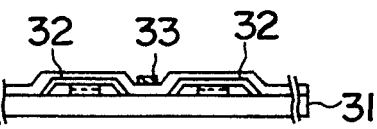
In FIG. 3, views A through J are cross-sectional views showing, in the order of steps, a fabrication process according to another embodiment of the present invention.
Figure 3B:
Figure 3C:
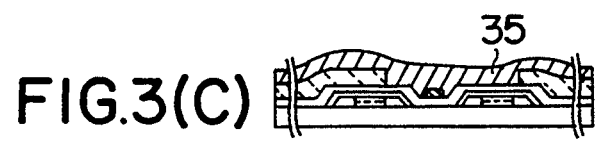
Figure 3D:
Figure 3E:
Figure 3F:
Figure 3G:
Figure 3H:
Figure 3I:
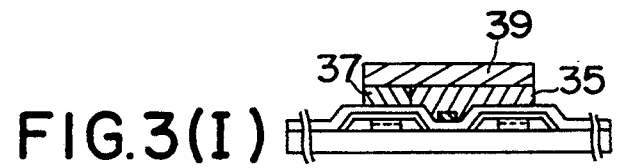
Figure 3J:
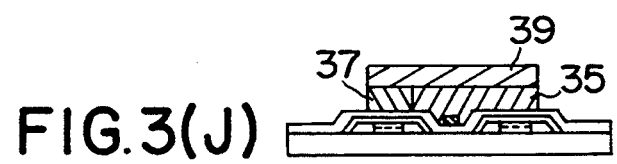

In the present invention, various transducer devices are usable as the electrochemical transducer devices as long as they can convert the quantity of a chemical change into an electrical quantity. Among these, ion-sensitive field effect transistors (ISFETs) are particularly preferred for their high sensitivity, low noise characteristic, excellent operational stability, and high feasibility to meet a demand for miniaturization. Further, amperometric electrodes are suited for the demand for mass-fabrication so that they can also be used preferably in the present invention.

It is preferred to use gold for the pseudo-reference electrode, although its material is not limited to gold.

No particular limitation is imposed on the material of the wafer. Any wafer can be satisfactorily used insofar as it is generally employed for the fabrication of an integrated circuit.

Regarding the photoresist, an ordinary photoresist can also be used satisfactorily. Any ordinary photoresist can be used as long as it permits effective application of the exposure, development and subsequent dissolving into solvent, preferably organic solvent such as acetone or methyl ethyl ketone (lift-off steps).

The enzyme-free liquid coating formulation of an enzyme-immobilizing crosslinkable polymer is spin-coated to provide a membrane so that an interaction between the immobilized enzyme and an environment, in which the biosensor is to be used, can be canceled out. The polymer is required to retain crosslinkability during the series of steps.

The present invention will hereinafter be described in detail with reference to the accompanying drawings.

EXAMPLE 1

Referring first to FIGS. 1(A) and 1(B), the glucose sensor makes use of an ion-sensitive field effect transistors (ISFETs).

Formed in each of two silicon islands on a sapphire substrate 1 are a source 2, a drain 3 and a gate 4. A silicon oxide film 5 is formed on each silicon island. Further, a silicon nitride film 6 is formed covering both the silicon oxide films 5 and an exposed surface of the sapphire substrate 1, whereby two ISFETs are constructed. The size of each gate 4 is 50 $\mu$m $\times$ 400 $\mu$m. Between the two ISFETs, a pseudo-reference electrode 7 is formed. Above one of the gates 4, a glucose-oxidase-immobilized membrane 8 is formed with the corresponding silicon oxide film 5 and the silicon nitride film 6 interposed therebetween. Above the other gate 4, an albumin-crosslinked membrane 9 is formed with the corresponding silicon oxide film 5 and the silicon nitride film 6 interposed therebetween. These membranes are covered by a permeation-restricted membrane 10. The size and thickness of the glucose-oxidase-immobilized membrane 8 are 100 $\mu$m $\times$ 500 $\mu$m and 1 $\mu$m, respectively. The size of the permeation-restricted membrane 10 is 800 $\mu$m $\times$ 500 $\mu$m. Its thickness is also 1 $\mu$m. This sensor chip is mounted on a flexible substrate 13 with its electrode pads 11 bonded to corresponding conductors by wires 12. The wirebonded portions are sealed by a waterproof wax 14. The size of this sensor chip is 1.7 mm $\times$ 4.7 mm. Determination is carried out by dipping a free end portion of the sensor chip in a sample.

In FIG. 2, views A through H correspond to the cross-sectional view of FIG. 1(B) and show, as the fabrication process according to the one embodiment of the present invention, the formation of a glucose-oxidase-immobilized membrane, an albumin-crosslinked membrane and a permeation-restricted membrane by photolithography.

The permeation-restricted membrane restricts permeation of a substrate, for example, glucose in an enzymatic reaction. Its final dry thickness can be easily controlled by applying a liquid coating formulation by spin-coating. Inclusion of a silicone is preferred because the resulting membrane becomes resistant to contamination while enjoying good compatibility with components in the body.

Gelation of the crosslinkable polymer is conducted prior to the subsequent lift-off step in which a solvent is employed.

Any lift-off technique can be satisfactorily applied as long as it is generally employed in the fabrication technology of integrated semiconductor circuits. Materials used by the lift-off technique, such as a solvent, should be selected in view of properties of biologically-acting components used in the biosensor, such as the enzyme.

Materials forming the enzyme-immobilized membrane should of course be selected in view of the properties of the enzyme. It is required to pay attention for the maintenance of stability of an enzymatic action, for example. In this respect, pH buffer capacity is required.

The protein used in the present invention is handled in the form of a liquid formulation during the series of operations. Therefore, the protein is preferably water-soluble. Further, the protein is desired to provide a crosslinked structure. Albumin is particularly preferred as it contains many amino groups.

To allow the crosslinkable polymer to undergo a photo-setting reaction, it is desired to use a compound, which can undergo a radical reaction, in the liquid coating formulation and to include a reaction initiator and a sensitizer in the liquid coating formulation. The photo-setting reaction can be conducted either singly or in combination with a chemical gelling reaction.

As shown in view A of FIG. 2, formed on a sapphire wafer 21 are ISFETs 22 and, via a silicon nitride film, a gold electrode 23 as a pseudo-reference electrode. As illustrated in view B, a positive photoresist 24 is coated over the entire surface of the wafer, exposed to ultraviolet rays through a photomask and then developed, whereby the photoresist are removed at predetermined areas. Next, as shown in view C, a 15 wt. % albumin-1 wt. % glutaraldehyde liquid coating formulation 25 is coated over the entire surface of the wafer and then caused to gel into an albumin-crosslinked membrane. A 25 wt. % silicone emulsion-15 wt. % albumin-1 wt. % glutaraldehyde liquid coating formulation 26 is then coated over the entire surface, followed by the gelation into a permeation-restricted membrane. Reference is next had to view D, in which the wafer is subjected to ultrasonic treatment in an organic solvent to dissolve the positive photoresist 24 so that the albumin-crosslinked membrane 25 and the permeation-restricted membrane 26 are allowed to remain at necessary areas. Referring next to view E, as in view B, the wafer with the albumin-crosslinked membrane 25 and the permeation-restricted membrane 26 formed thereon is coated with a positive photoresist 27, followed by the removal of the positive photoresist 27 at predetermined areas. Further, as shown in view F, a 15 wt. % albumin-1 wt. % glutaraldehyde liquid coating formulation 28 containing 6 wt. % of glucose oxidase is coated on the resulting wafer and caused to gel and, then, a 25 wt. % silicone emulsion-15 wt. % albumin-1 wt. % glutaraldehyde liquid coating formulation 29 is coated and caused to gel. Reference is next made to view G, in which the positive photoresist is dissolved as in view D so that the glucose-oxidase-immobilized membrane 28 and the permeation-restricted membrane 29 are allowed to remain only at necessary areas. Next, as shown in view H, the wafer on which the albumin-crosslinked membrane 25, the glucose-oxidase-immobilized membrane 28 and the permeation-restricted membranes 26,29 are formed is cut into pieces functional unit by functional unit, thereby obtaining chips similar to the glucose sensor described above with reference to FIGS. 1(A) and 1(B).

Glucose sensors have heretofore been fabricated one by one. The non-defective percentage of such glucose sensors was 10% or less. The process of this example has however attained a non-defective percentage as high as 90% or even better.

EXAMPLE 2

As another example of the present invention, the procedures of Example 1 are repeated except that a 50 wt. % amino-modified silicone-5 wt. % glutaraldehyde liquid coating formulation is coated instead of each 25 wt. % silicone emulsion-15 wt. % albumin-1 wt. % glutaraldehyde liquid coating formulation. In this example, very dense and thin permeation-restricted membranes can be obtained.

EXAMPLE 3

In FIG. 3, views A through J correspond to the cross-sectional view of FIG. 1(B) like views A through H in FIG. 2 and show a fabrication process according to another embodiment of the present invention. First, as illustrated in view A, formed on a sapphire wafer 31 are ISFETs 32 and, via a silicon nitride film, a gold electrode 33 as a pseudo-reference electrode. As illustrated in view B, a positive photoresist 34 is coated over the entire surface of the wafer, exposed to ultraviolet rays through a photomask and then developed, whereby the photoresist are removed at predetermined areas. Next, as shown in view C, a 15 wt. % albumin-1 wt. % glutaraldehyde liquid coating formulation 35 is coated over the entire surface of the wafer and then caused to gel. As illustrated in view D, the wafer is next subjected to ultrasonic treatment in an organic solvent to dissolve the positive photoresist, whereby an albumin-crosslinked membrane 35 is formed. Reference is next had to view E in which, as in view B, the wafer with the albumin-crosslinked membrane 35 formed thereon is coated with a positive photoresist 36, followed by its removal at predetermined areas. Next, as depicted in view F, a 15 wt. % albumin-1 wt. % glutaraldehyde liquid coating formulation 37 containing 6 wt. % of glucose oxidase is coated over the wafer and then caused to gel. Then, as illustrated in figure G, the positive photoresist 36 is dissolved as in view D so that a glucose-oxidase-immobilized membrane 37 is formed. Reference is now made to view H, the resulting wafer is coated with a radical-reactive silicone emulsion 38 which contains 1 wt. % of riboflavin phosphate as a reaction initiator and 1 wt. % of tetramethylenediamine as a photosensitizer. Next, as illustrated in view I, the emulsion 38 is exposed to ultraviolet rays through a photomask and then developed, so that a permeation-restricted membrane 39 is formed at a desired area. Next, as shown in view J, the wafer on which the albumin-crosslinked membrane 35, the glucose-oxidase-immobilized membrane 37 and the permeation-restricted membrane 39 are formed is cut into pieces functional unit by functional unit, thereby obtaining chips similar to the glucose sensor described above with reference to FIGS. 1(A) and 1(B).

Although more steps are needed in this embodiment, it is relatively easy to control the thickness of the permeation-restricted membrane by changing the concentration of the silicone emulsion 38 from 0.1 to 5 wt. %.

EXAMPLE 4

Figure 4A:
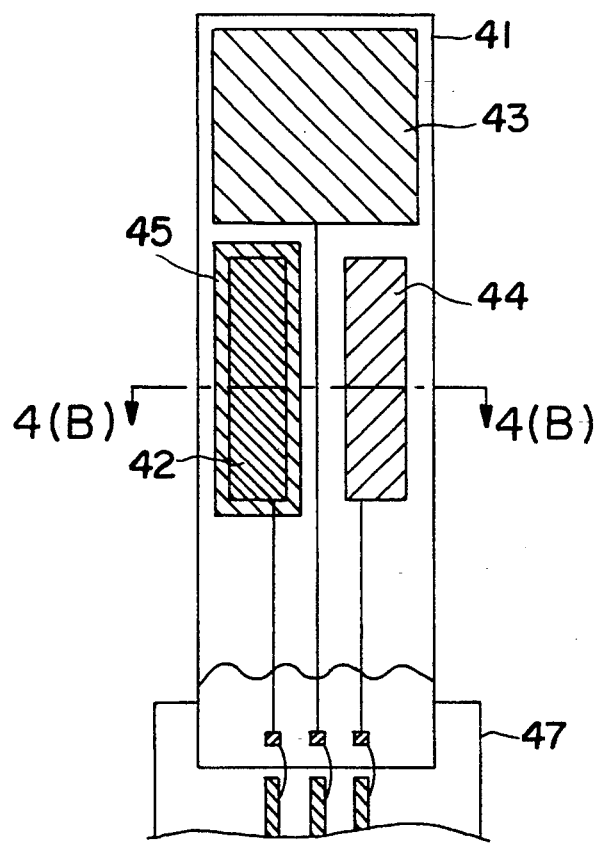
FIG. 4(A) is a schematic illustration depicting a glucose sensor fabricated by a process according to a further embodiment of the present invention.
Figure 4B:
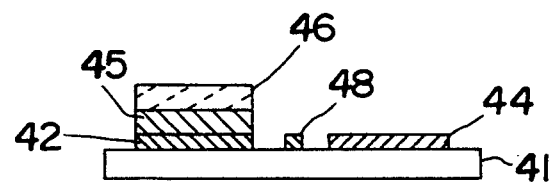
FIG. 4(B) is a cross-sectional view of the glucose sensor taken in the direction of arrows IV(B)—IV(B) of FIG. 4(A)
Figure 5:
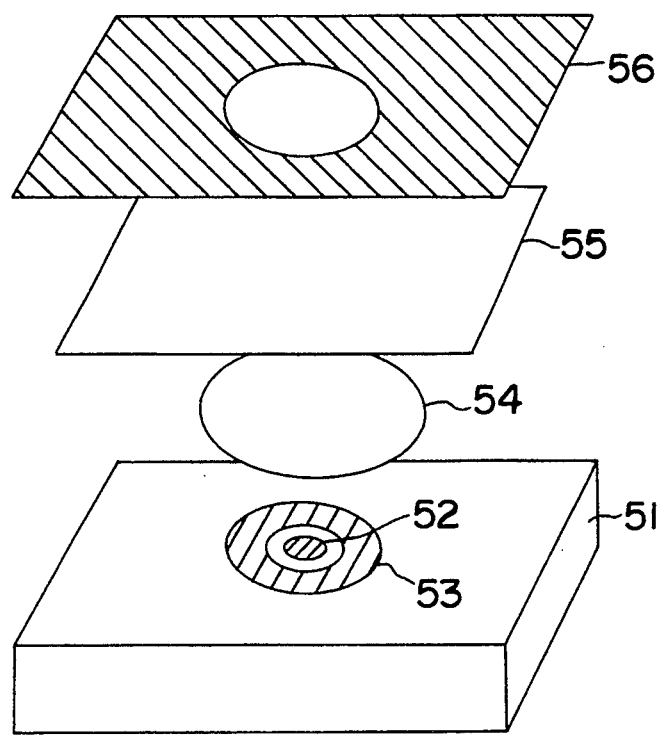
FIG. 5 is an exploded, schematic view of a glucose sensor fabricated in accordance with a conventional process.
Figure 6A:
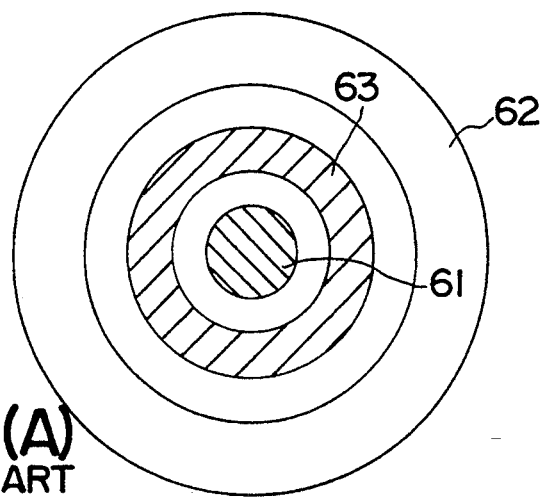
FIGS. 6(A) and 6(B) are schematic illustrations of a glucose sensor fabricated in accordance with another conventional process.
Figure 6B:
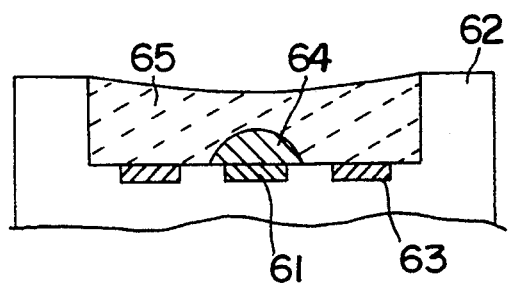

FIGS. 4(A) and 4(B) illustrate the process according to the further embodiment of the present invention. A working electrode 42 and a counter electrode 43 are formed by patterning gold or platinum on a silicon wafer 41. Further, a reference electrode 44 is formed by patterning silver and treating it with a solution of ferric chloride ($FeCl_3$). Then, a glucose-oxidase-immobilized membrane 45 and a permeation-restricted membrane 46 are patterned by photolithography. The wafer so obtained is finally cut chip by chip. Each chip is then mounted on a flexible substrate 47. Similarly to the foregoing examples in which ISFETs were employed, the permeation-restricted membrane 46 can be formed by any one of the methods in which a 25 wt. % silicone emulsion-15 wt. % albumin-1 wt. % glutaraldehyde liquid coating formulation, a 50 wt. % amino-modified silicone-5 wt. % glutaraldehyde liquid coating formulation and a radical-modified silicone emulsion are used, respectively.

Operation

Figure 7:
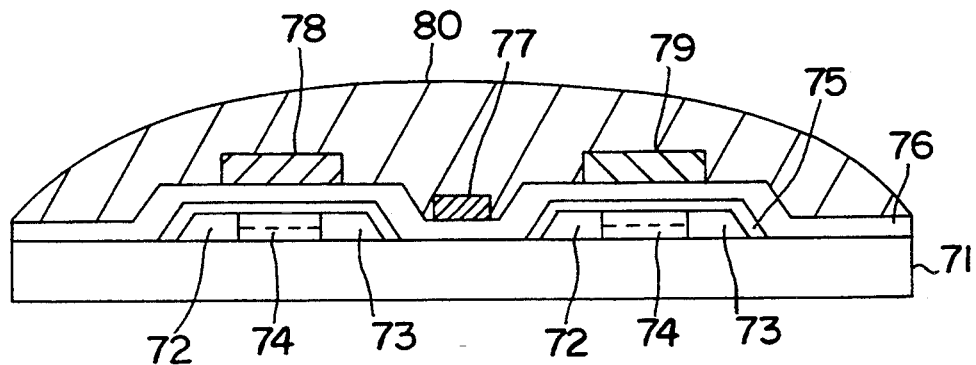
FIG. 7 is a cross-sectional view of a glucose sensor obtained by practicing the present invention.

Referring next to FIG. 7, a description will next be made of operation of a functional device obtained by practicing the present invention. The functional device shown in FIG. 7 is merely illustrative. FIG. 7 shall therefore not be interpreted as showing all products available from practicing the present invention. Formed in each of two silicon islands on a sapphire substrate 71 are a source 72, a drain 73 and a gate 74. A silicon oxide film 75 is formed on each silicon island. Further, a silicon nitride film 76 is formed covering both the silicon oxide films 75 and an exposed surface of the sapphire substrate 71, whereby two ion-sensitive field effect transistors (ISFETs) are constructed. Further, a gold electrode 77 is formed between the two ISFETs. A glucose-oxidase-immobilized membrane 78 is formed above one of the gates 74, while an albumin-crosslinked membrane 79 is formed above the other gate 74. These membranes are covered by a permeation-restricted membrane 80. Upon determination of the concentration of glucose in blood by the above sensor, glucose which has permeated through the permeation-restricted membrane 80 is converted to gluconic acid within the glucose-oxidase-immobilized membrane 78. The gluconic acid then reaches a surface of the corresponding ISFET. As the ISFET functions as a pH sensor, measurement of a pH variation result from the formation of gluconic acid makes it possible to determine the glucose concentration. The permeation-restricted membrane 80 restricts the permeation of glucose so that the measurable upper limit of the sensor is shifted upwardly. The cross-sectional shape of the permeation-restricted membrane 80 is merely illustrative. The other ISFET above which the albumin-crosslinked membrane 79 is formed functions as a reference ISFET and corrects a drift or the like of a response of the sensor.

As has been described above, the process according to the present invention can fabricate a large quantity of products of uniform characteristics without particular difficulty. An appropriate selection of materials to be used allows to apply the process of the present invention for the fabrication of various biosensors including not only enzyme sensors but also immune response sensors.

What is claimed is:

1. A process for the fabrication of plural biosensors having uniform response characteristics and a wide response range, each of said biosensors having at least two pairs of electrochemical transducer devices and a pseudo-reference electrode located substantially at a midpoint between said at least two pairs of electrochemical transducer devices, said devices and said electrode being both formed on one side of a wafer, and also an enzyme-immobilized membrane and a permeation-restricted membrane, both arranged over said devices and said electrode, which comprises:
   1) covering said wafer with a first photoresist coating film except for surfaces of one of said devices and of said electrode;
   2) spin-coating said surfaces with an enzyme-free liquid coating formulation of an enzyme-immobilizing crosslinkable polymer;
   3) spin-coating the resulting structure further with a first permeation-restricted-membrane-forming liquid coating formulation of a crosslinkable polymer;
   4) causing said enzyme-free liquid coating formulation and said first permeation-restricted-membrane-forming liquid coating formulation to gel, whereby first and second gelled membranes are formed in a stacked form;
   5) dissolving said first photoresist coating film with portions of said first and second gelled membranes which have been formed on said first photoresist coating film, whereby said first and second gelled membranes remain in the stacked form only on said surfaces of said one device and said electrode and a partly coated wafer is obtained;
   6) covering a surface of the partly-coated wafer with a second photoresist coating film except for a surface of the other device;
   7) spin-coating said surface of said other device with an enzyme-containing liquid coating formulation of an enzyme-immobilizing crosslinkable polymer;
   8) spin-coating the spin-coated surface of said other device further with a second permeation-restricted-membrane-forming liquid coating formulation of a crosslinkable polymer;
   9) causing said enzyme-containing liquid coating formulation and said second permeation-restricted-membrane-forming liquid coating formulation to gel, whereby third and fourth gelled membranes are formed in a stacked form;
   10) dissolving said second photoresist coating film with said third and fourth gelled membranes which have been formed on said second photoresist coating into solvent, whereby a structure is obtained wherein said third and fourth gelled membranes remain only on said surface of said other device; and then
   11) cutting the structure into pieces so that each piece includes parts of said paired electrochemical transducer devices and a part of said pseudo-reference electrode, with said electrode being located substantially at the midpoint between the parts.

2. A process according to claim 1, wherein each of said first and second permeation-restricted-membrane-forming liquid coating formulations is a silicone-containing liquid coating formulation of a protein and a crosslinking agent.

3. A process according to claim 2, wherein said protein is albumin.

4. A process according to claim 1, wherein each of said first and second permeation-restricted-membraneforming liquid coating formulations is a liquid coating formulation of an amino-modified silicone and a crosslinking agent.

5. A process according to claim 1, wherein each of said devices is an ion-sensitive field effect transistor.

6. A process according to claim 1, wherein each of said devices is an amperometric electrode.

7. A process according to claim 1, wherein the enzyme in said enzyme-containing liquid coating formulation is glucose oxidase.

8. A process according to claim 1, wherein each enzyme-free liquid coating formulation of the enzyme-immobilizing crosslinkable polymer is a liquid coating formulation containing a protein and a crosslinking agent.

9. A process for the fabrication of plural biosensors having uniform response characteristics and a wide response range, each of said biosensors having at least two pairs of electrochemical transducer devices and a pseudo-reference electrode located substantially at a midpoint between said at least two pairs of electrochemical transducer devices, said devices and said electrode being both formed on one side of a wafer, and also an enzyme-immobilized membrane and a permeation-restricted membrane, both arranged over said devices and said electrode, which comprises:

1) covering said wafer with a first photoresist coating film except for surfaces of one of said devices and of said electrode;
2) spin-coating said surfaces with an enzyme-free liquid coating formulation of an enzyme-immobilizing cross-linkable polymer and then causing said enzyme-free liquid coating formulation to gel, whereby a first gelled membrane is formed;
3) dissolving said first photoresist coating film with a portion of said first gelled membrane which has been formed on said first photoresist coating film, whereby said first gelled membrane remains only on said surfaces of said one device and said electrode and a partly coated wafer is obtained;
4) covering a surface of the partly-coated wafer with a second photoresist coating film by a lithographic technique except for a surface of the other device;
5) spin-coating said surface of said other device with an enzyme-containing liquid coating formulation of an enzyme-immobilizing crosslinkable polymer;
6) dissolving said second photoresist coating film with said enzyme-containing liquid coating formulation of an enzyme-immobilizing crosslinkable polymer, whereby a first structure is obtained wherein said enzyme-immobilizing crosslinkable polymer remains only on said surface of said other device;
7) spin-coating the first structure further with a permeation-restricted-membrane-forming liquid coating formulation of a photocrosslinkable polymer;
8) photopolymerizing the coated permeation-restricted-membrane-forming liquid coating formulation by a photolithographic technique followed by dissolving unpolymerized coating formulation, whereby a second structure is obtained wherein a gelled membrane is formed only on said remaining first gelled membrane and enzyme-immobilizing photocrosslinkable polymer in a stacked form; and
9) cutting the second structure into pieces so that each piece includes parts of said paired electrochemical transducer devices and a part of said pseudo-reference electrode, with said electrode being located substantially at the midpoint between the parts.

10. A process according to claim 9, wherein said permeation-restricted-membrane-forming liquid coating formulation is a silicone emulsion containing a protein and a crosslinking agent.

11. A process according to claim 10, wherein said protein is albumin.

12. A process according to claim 9, wherein said liquid coating formulation of said permeation-restricted-membrane-forming crosslinkable polymer further comprises a reaction initiator and a sensitizer.

13. A process according to claim 9, wherein each of said devices is an ion-sensitive field effect transistor.

14. A process according to claim 9, wherein each of said devices is an amperometric electrode.

15. A process according to claim 9, wherein the enzyme in said enzyme-containing liquid coating formulation is glucose oxidase.

16. A process according to claim 9, wherein each enzyme-free liquid coating formulation of the enzyme-immobilizing crosslinkable polymer is a protein solution containing a crosslinking agent.

* * * * *